United States Patent [19]
Kohler et al.

[11] Patent Number: 5,466,927
[45] Date of Patent: Nov. 14, 1995

[54] INSPECTION OF TRANSLUCENT CONTAINERS

[75] Inventors: Timothy A. Kohler; James A. Ringlien, both of Maumee, Ohio

[73] Assignee: Owens-Brockway Glass Container Inc., Toledo, Ohio

[21] Appl. No.: 224,208

[22] Filed: Apr. 8, 1994

[51] Int. Cl.$^6$ .............................. G01N 21/41; B07C 5/00
[52] U.S. Cl. .................. 250/223 B; 356/240; 209/526
[58] Field of Search ................... 250/223 B, 227.29, 250/556, 227.28; 356/240, 428, 371, 427; 209/524, 526, 558

[56] References Cited

U.S. PATENT DOCUMENTS

| | | | |
|---|---|---|---|
| 3,758,215 | 9/1973 | Paroulo et al. | 356/196 |
| 4,083,637 | 4/1978 | Ellinger et al. | 356/240 |
| 4,175,236 | 11/1979 | Juvinall | 250/566 |
| 4,256,957 | 3/1981 | Ford et al. | 250/223 B |
| 4,262,196 | 4/1981 | Smith | 250/223 B |
| 4,428,673 | 1/1984 | Yoshida | 356/240 |
| 4,448,526 | 5/1984 | Miyazawa | 356/237 |
| 4,459,023 | 7/1984 | Reich et al. | 356/237 |
| 4,551,627 | 11/1985 | Reich | 250/339 |
| 4,601,395 | 7/1986 | Juvinall | 209/526 |
| 4,608,709 | 8/1986 | Hedler et al. | 382/1 |
| 4,948,956 | 8/1990 | Fukuchi | 250/223 B |
| 4,959,537 | 9/1990 | Kimoto et al. | 250/223 B |
| 4,983,822 | 1/1991 | Fukuchi | 250/223 B |
| 5,102,227 | 4/1992 | Zwirner et al. | 356/384 |
| 5,243,400 | 9/1993 | Ringlien | 356/240 |

*Primary Examiner*—Edward P. Westin
*Assistant Examiner*—Jacqueline M. Steady

[57] ABSTRACT

Apparatus for inspecting the bottom of a container that includes a light sensor positioned to view the container bottom through the open container mouth, a light source positioned externally of the container on the opposite side of the container bottom, and electronics for detecting commercial variations in the container bottom as a function of light energy incident on the sensor. The light source, as viewed by the sensor through the container bottom, is characterized by being elongated radially of the container bottom and narrow transversely of the container bottom. In this way, any variations in the container bottom that refract the line of sight of the sensor in the radial direction, such as mold code rings and baffle scars, are essentially transparent as viewed by the sensor. On the other hand, variations that refract the sensor line of sight laterally of the container bottom, such as glass particles, knots and lumps, produce a dark image at the sensor since the sensor cannot see the light source through the variation.

8 Claims, 2 Drawing Sheets

INSPECTION OF TRANSLUCENT CONTAINERS

The present invention is directed to inspection of translucent containers for commercial variations that affect optical properties of the container walls, and more particularly to an apparatus and method for inspecting the bottom of a container through the container mouth.

BACKGROUND AND OBJECTS OF THE INVENTION

In the manufacture of translucent containers such as clear or colored glass bottles and jars, various types of checks or other commercial variations can occur in the walls of the containers. For example, glass particles, knots and lumps, and opaque stones or other occlusions can occur in the container bottom (i.e., the container base and heel) that affect commercial desirability of the container. On the other hand, baffle scars can occur in the container bottom without affecting commercial acceptability of the containers, and code rings can be molded into the container bottom for optically associating the container with its mold of origin. It is therefore desirable on the one hand to provide an inspection technique for detecting and quantifying potentially undesirable variations such as stones, glass particles, knots and lumps, while at the same time substantially ignoring mold code rings and variations such as baffle scars that do not affect commercial acceptability of the container.

It has heretofore been proposed to employ electro-optical inspection systems for detecting commercial variations that affect optical properties of the container. The basic principle is that a light source is positioned on one side of the container and a camera is positioned on the other. The light source may be configured to have an intensity that varies across one dimension of the source. Light rays normally travel from the source straight through the container wall and are then focused onto the camera, and are viewed by the camera at a given intensity. However, a refractive commercial variation bends the light ray as it travels through the container wall, so that the image projected onto the camera is of a different area of the light source. If such different area has a different intensity than the area normally imaged onto the camera, the camera can detect the refractive site. An opaque site such as a stone blocks transmission of light through the container wall, and can therefore be detected as a dark spot against a light background.

U.S. Pat. No. 5,243,400, assigned to the assignee hereof, discloses a technique for varying the effective intensity of the light source across the light source. A light control film is positioned adjacent to the light source between the light source and the container, and comprises a plurality of parallel slats spaced from each other so as to limit the angle from which the image of the light source can be viewed by the camera. Commercial variations are detected as a function of variations in light intensity received at the camera. Any refractive variation in the container wall refracts or bends the line of sight of the camera at an angle to the camera axis. As this angle increases, the slats progressively obstruct the light source, until the camera can no longer see the light source at the critical viewing angle of the slats.

SUMMARY OF THE INVENTION

Apparatus for inspecting the bottom of a container in accordance with the presently preferred embodiments of the invention includes a light sensor positioned to view the container bottom through the open container mouth, a light source positioned externally of the container on the opposite side of the container bottom, and electronics for detecting commercial variations in the container bottom as a function of light energy incident on the sensor. The light source, as viewed by the sensor through the container bottom, is characterized by being elongated in one direction relative to the container bottom—i.e., in the radial direction—and narrow in the transverse direction. In this way, any variations in the container bottom that refract the line of sight of the sensor in the radial direction, such as mold code rings and baffle scars, are essentially transparent as viewed by the sensor. On the other hand, variations that refract the sensor line of sight laterally of the container bottom, such as glass particles, knots and lumps, produce a dark image at the sensor since the sensor cannot see the light source through the variation.

The light source in the preferred embodiments is constructed to be characterized by an elongate radial dimension and narrow lateral dimension by either constructing the light source to be physically long and narrow, or by employing a light control film as in the above-noted U.S. Patent with parallel slats extending radially of the container bottom. In either embodiment, the light source is characterized by a wide illumination angle radially of the container bottom and a narrow illumination angle transversely of the container bottom. Preferably, the light source extends across the entire diameter of the container bottom, and the light sensor comprises a line scan camera having an array of light sensitive elements that receive an image of the container bottom as illuminated by the light source across the entire diameter of the container bottom (i.e., including the base and heel). The container is rotated during inspection about its central axis, and the sensor array is scanned at increments of container rotation to develop a two-dimensional image of the container bottom. This image may be analyzed for refractive and opaque commercial variations employing otherwise conventional techniques.

BRIEF DESCRIPTION OF THE DRAWINGS

The invention, together with additional objects, features and advantages thereof, will be best understood from the following description, the appended claims and the accompanying drawings in which:

DETAILED DESCRIPTION OF PREFERRED EMBODIMENTS

Figure 2:
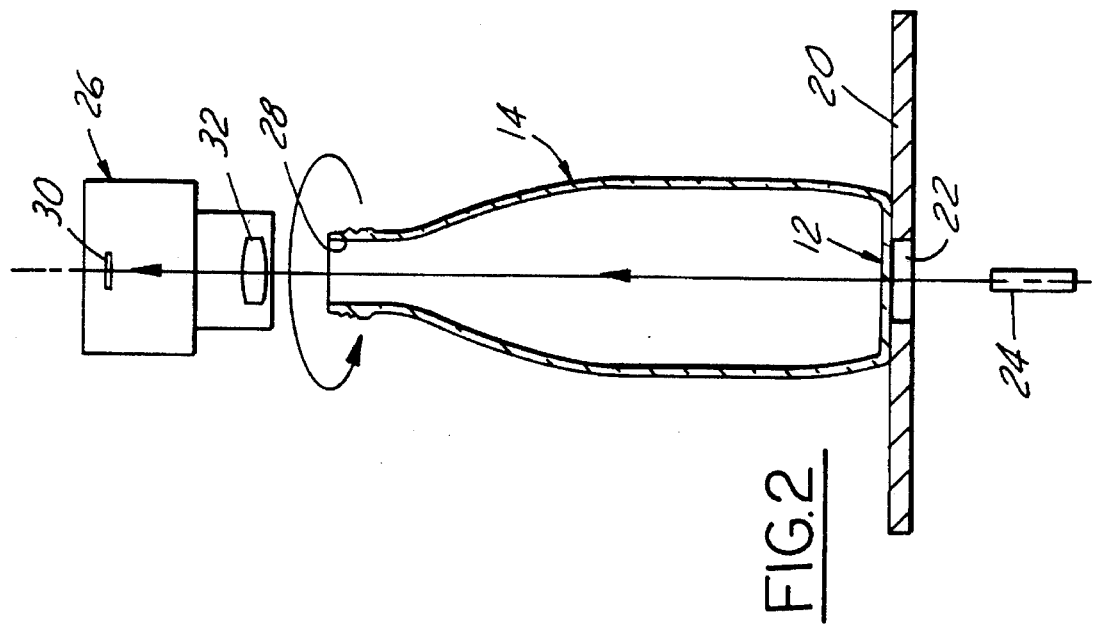
FIG. 2 is a fragmentary side view of the inspection apparatus of FIG. 1.
Figure 1:
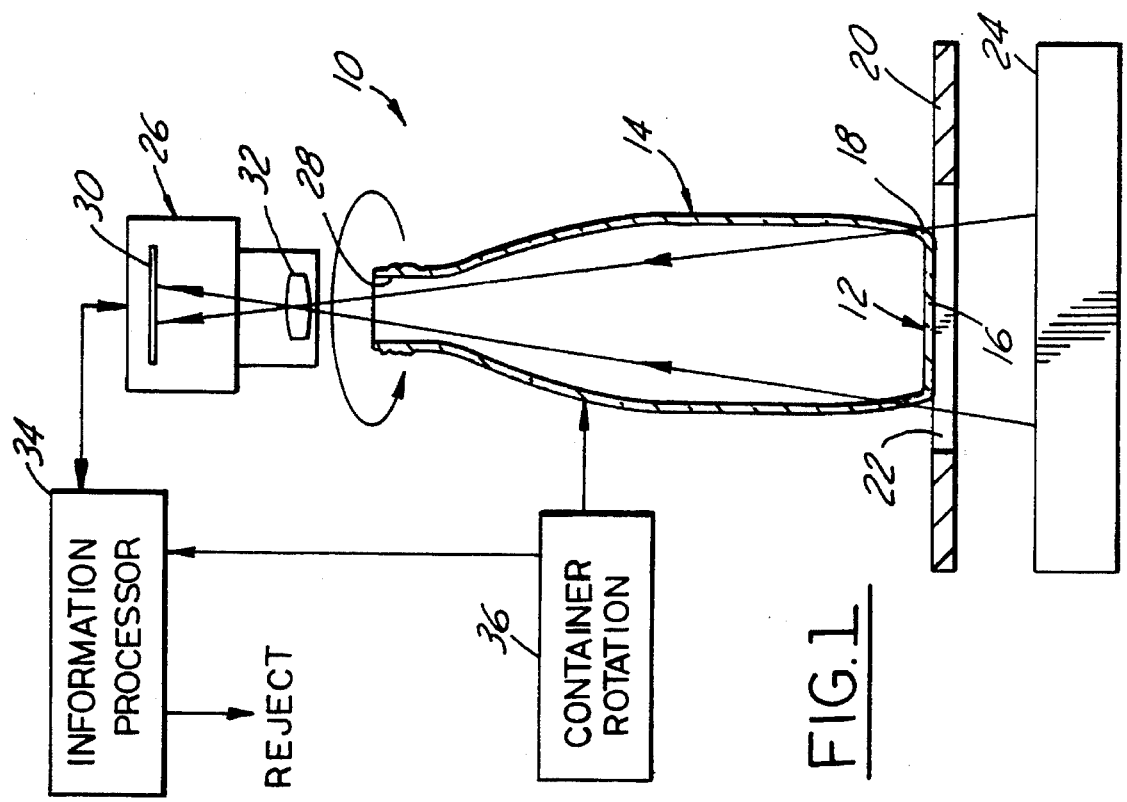
FIG. 1 is an electro-optical schematic diagram that illustrates one presently preferred embodiment of the invention.

FIGS. 1 and 2 illustrate inspection station apparatus 10 for inspecting the bottoms 12 of a translucent containers 14—i.e., the base 16 and heel 18 of containers 14. Sequential containers 14 are brought to the inspection station of apparatus 10 by a starwheel conveyor or the like that moves the container along a slide plate 20 into registry with a slot 22. A light source 24 is positioned beneath slide plate 20 to illuminate container bottom 12 through slot 22. A line scan camera 26 is positioned above container 14 in apparatus 10 to view bottom 12 of container 14 through the open container mouth 28, and thus to view the image of light source 24 through the container bottom and slide plate slot 22.

Figure 3:
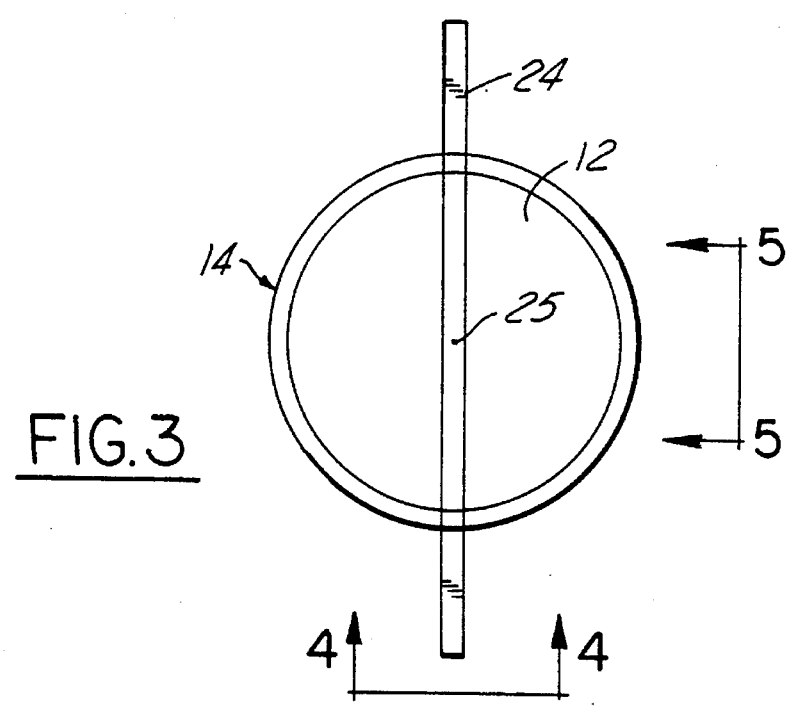
FIG. 3 is a plan view of the container bottom and light source in FIGS. 1 and 2 as viewed by the camera.

Light source 24 is long and thin, as best seen by comparing FIGS. 1 and 2, with the elongated dimension of light source 24 extending diametrically across the container bottom intersecting the container axis 25 (FIG. 3). Light source 24 may comprise an elongated incandescent lamp or a series of individual lamps that illuminate the bottom of container 14 through a diffuser. Line scan camera 26 includes a linear array sensor 30 having a plurality of light sensing elements disposed along a line parallel to the elongated dimension of light source 24 and intersecting the container axis. A lens 32 focuses the image of container bottom 12, as illuminated by light source 24, onto linear array sensor 30, viewed through open mouth 28 of container 14. Container 14 in apparatus 10 is engaged by a suitable mechanism 36 for rotating the container about its central axis 25. Camera 26 is coupled to an information processor 34 for scanning sensor 30 at increments of container rotation.

Figure 4:
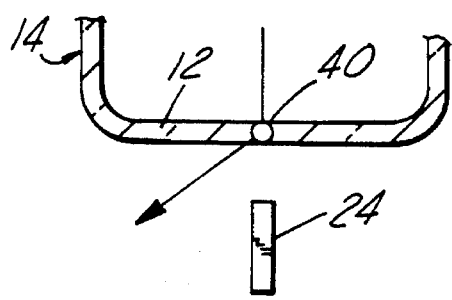
FIGS. 4 and 5 are fragmentary schematic diagrams, respectively similar to portions of FIGS. 2 and 1, that illustrate operation of the invention.
Figure 5:
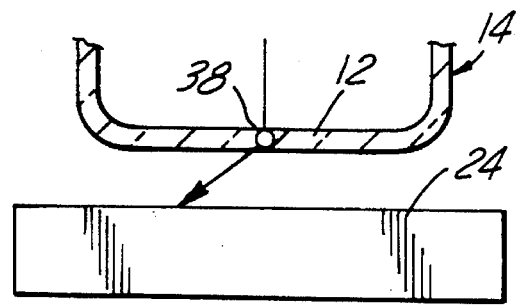

Operation of the embodiment of FIGS. 1 and 2 is illustrated in FIGS. 3–5. FIG. 3 illustrates the geometry of light source 24 relative to container bottom 12, being elongated diametrically of the container and narrow laterally of the container as noted above. When a refractive variation 38 (FIG. 5) that refracts the camera line of sight essentially in a radial direction, such as a baffle scar or mold code ring, enters the camera field of view, the refractive variation does not affect intensity of light incident on the sensor because the sensor will still see the light source because of its elongated dimension in the radial direction. On the other hand, when a refractive variation 40 (FIG. 4) of the type that refracts the camera line of sight laterally of the container diameter, such as a glass particle, knot or lump, enters the camera field of view, the line of sight of at least some of the camera elements is refracted away from the light source as illustrated at FIG. 4. Camera sensor 30 is scanned by information processor 34 at increments of container rotation to develop a two-dimensional image of the entire container bottom. Refractive variations 40 (as well as opaque variations such as stones) will appear in such image as dark spots or areas against an otherwise light background. The image may be analyzed employing conventional techniques, such as shown in U.S. Pat. No. 4,601,395 for example, and information processor 34 generates a reject signal to remove container 14 from the process line in the event that any or all of the refractive variations 40 (and opaque variations) exceed acceptable specifications.

Figure 6:
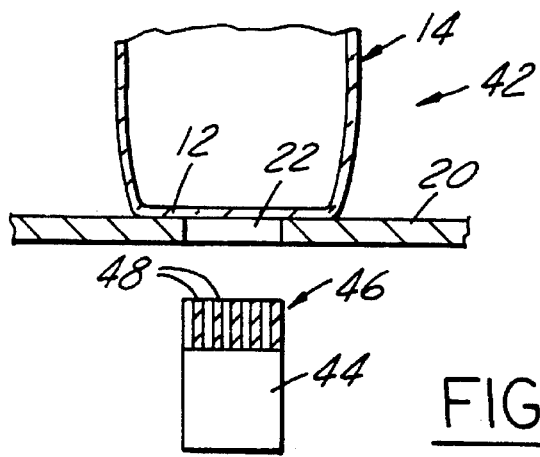
FIG. 6 is a fragmentary schematic diagram similar to that of FIG. 2 but showing a modified embodiment of the invention.

FIG. 6 illustrates a modified apparatus 42 in accordance with the present invention, in which the light source 44 is made narrow in the lateral direction by means of a light control film 46 having a plurality of spaced parallel slats 48 extending diametrically across the bottom 12 of container 14. Any variations 38 (FIG. 5) that refract the camera line of sight in the radial direction will not affect the camera image of the container bottom because the refraction is in a direction parallel to slats 48. However, any variation 40 (FIG. 4) that refracts the camera line of sight laterally of the light source will cause progressive obstruction of the light source as seen by the camera, until the camera can no longer see the light source through the container bottom at the critical viewing angle of the slats. Thus, the embodiment of FIGS. 1–5 cause the image to be either bright or dark when the camera line of sight is refracted off of the light source, while the embodiment of FIG. 6 provides levels of gray between an unobstructed view of the light source and a completely obstructed view of the light source at the critical viewing angle of the light control film slats.

We claim:

1. Apparatus for inspecting the bottom of a container having an open mouth and a central axis, said apparatus comprising:

light sensing means positioned to view the container bottom through the container mouth, a light source positioned externally of the container on a side of the container bottom opposite the container mouth, said light source as viewed by said light sensing means through the container bottom being characterized by having an illumination angle radially of the container bottom such that variations in the container bottom that refract light radially of the container bottom are transparent as viewed by said light sensing means through the container mouth and an illumination angle transversely of the container bottom such that variations in the container bottom that refract light laterally of the container bottom produce a dark image at said light sensing means, and means for detecting commercial variations in the container bottom as a function of light energy incident on said sensing means.

2. The apparatus set forth in claim 1 wherein said illumination angle radially of the container bottom extends diametrically across the container bottom.

3. The apparatus set forth in claim 1 wherein said light source includes a plurality of parallel slats extending radially of the container bottom spaced from each other so as to limit the lateral angle from what the image of said light source can be viewed at said sensing means.

4. The apparatus set forth in claim 1 further comprising means for rotating the container about its central axis.

5. The apparatus set forth in claim 4 wherein said light sensing means comprises an array sensor having a plurality of sensing elements disposed in an array that extends radially of the container, and wherein said variations-detecting means comprises means for scanning said array at increments of container rotation to develop a two-dimensional image of the container bottom.

6. A method of inspecting the bottom of a container having an open mouth and a central axis, said method comprising the steps of:

(a) positioning a light sensor to view the container bottom through the container mouth, (b) illuminating the container bottom with a light source externally of the container in axial alignment with said sensor in such a way that the image of the light source has a dimension laterally of the container bottom such that any laterally refractive variations in the container bottom refract the line of sight of the sensor laterally away from said light source, and (c) detecting commercial variations in the bottom of the container as a function of intensity of light energy incident on said sensor from said source through the bottom.

7. The method set forth in claim 6 comprising the additional step of:

(d) rotating the container about its axis while performing said steps (a) and (b).

8. Apparatus for inspecting the bottom of a container having an open mouth and a central axis, said apparatus comprising:

light sensing means positioned to view the container bottom through the container mouth, a light source positioned externally of the container on a side of the container bottom opposite the container mouth, said light source being characterized by an illumination angle radially of the container bottom such that variations in the container bottom that refract light radially of the container bottom are transparent as viewed by said light sensing means through the container mouth and an illumination angle transversely of the container bottom such that variations in the container bottom that refract light laterally of the container bottom produce a dark image at said light sensing means, and means for detecting commercial variation in the container bottom as a function of light energy incident on said sensing means.

* * * * *